(12) United States Patent
McKelvey

(10) Patent No.: US 7,335,236 B2
(45) Date of Patent: Feb. 26, 2008

(54) ENHANCING THE COLOUR PERCEPTION OF ARTIFICIALLY COLOURED HAIR

(75) Inventor: Graham Neil McKelvey, Farnborough (GB)

(73) Assignee: The Procter & Gamble Company, Cincinnati, OH (US)

( * ) Notice: Subject to any disclaimer, the term of this patent is extended or adjusted under 35 U.S.C. 154(b) by 251 days.

(21) Appl. No.: 11/013,669

(22) Filed: Dec. 16, 2004

(65) Prior Publication Data

US 2005/0132506 A1 Jun. 23, 2005

(30) Foreign Application Priority Data

Dec. 18, 2003 (EP) ................................ 03258020.1

(51) Int. Cl.
*A61K 7/13* (2006.01)
(52) U.S. Cl. ........................ 8/405; 8/431; 8/435; 8/552; 8/581; 8/632; 424/70.2
(58) Field of Classification Search ................... 8/405, 8/431, 435, 552, 581, 632; 424/70.2
See application file for complete search history.

(56) References Cited

U.S. PATENT DOCUMENTS

| | | | |
|---|---|---|---|
| 5,792,825 A | 8/1998 | Karrer | |
| 6,824,764 B2 | 11/2004 | Devin-Baudoin | |
| 6,824,765 B2 | 11/2004 | Gawtrey | |
| 6,846,333 B2 | 1/2005 | Legrand | |
| 6,953,484 B2 | 10/2005 | Devin-Baudoin | |
| 2002/0114771 A1 | 8/2002 | Nakanishi | |
| 2002/0187117 A1* | 12/2002 | Devin-Baudoin et al. | .. 424/70.2 |
| 2003/0129155 A1 | 7/2003 | Devin-Baudoin | |
| 2003/0223946 A1* | 12/2003 | Glenn et al. | ............. 424/70.12 |
| 2004/0045098 A1* | 3/2004 | Lazzeri | ........................ 8/405 |

FOREIGN PATENT DOCUMENTS

| | | |
|---|---|---|
| GB | 2138845 A | 10/1984 |
| JP | 57192310 A | 11/1982 |
| JP | 63051314 A | 3/1988 |
| JP | 63051315 A | 3/1988 |
| WO | WO-99/66793 A1 | 12/1999 |

OTHER PUBLICATIONS

STIC Search Report dated Dec. 14, 2006.*

* cited by examiner

*Primary Examiner*—Eisa Elhilo
(74) *Attorney, Agent, or Firm*—Melissa G. Krasovec; Marianne Dressman

(57) ABSTRACT

The invention herein encompasses the use of aminosilicones to enhance the colour perception of artificially coloured hair. Also encompassed are compositions, a method of use, a kit-of-parts and an article of manufacture.

16 Claims, No Drawings

ENHANCING THE COLOUR PERCEPTION OF ARTIFICIALLY COLOURED HAIR

TECHNICAL FIELD OF THE INVENTION

The present invention relates to the colouring of hair. The invention herein enhances the colour perception of artificially coloured hair.

BACKGROUND OF THE INVENTION

The artificial colouring of hair is abundantly described in the prior art, and a great variety of shades are commercially available to that effect as hair colouring kits. While consumers are satisfied with the degree of choice that these different shades offer, there is an overall need for providing more intense colours in a durable manner.

Instead of embarking on further research to identify new dye molecules, the inventors herein have found that applying aminosilicones onto the hair after it has been artificially coloured, provides a durably enhanced colour perception of the artificially coloured hair.

The use of aminosilicones is well known in this field—see for instance EP 1 312 342 and EP 1 312 350, but it has never been reported that the application of those silicones to the hair after it has been artificially coloured provides a durable enhancement of the colour perception of the coloured hair.

Silicones are generally formulated as emulsions, however the inventors have furthermore found that the benefit and its duration are maximised if the silicone used is provided as a composition that is a solution of the aminosilicone.

SUMMARY OF THE INVENTION

In a first embodiment, the present invention encompasses the use of an aminosilicone for providing enhanced colour perception of artificially coloured hair.

In a second embodiment, the present invention encompasses a composition that is a solution of an aminosilicone.

In a third embodiment, the present invention encompasses a method of enhancing the colour perception of artificially coloured hair, comprising the steps of applying onto said coloured hair a composition which is a solution of an aminosilicone.

In a fourth embodiment, the present invention encompasses a kit of parts comprising one or several first components for colouring hair and a second component for enhancing the colour perception of the hair coloured with said first component(s), where said second component is a solution of an aminosilicone according to the above formula.

In a fifth embodiment, the present invention encompasses an article of manufacture which is suitable for use herein, for instance as a second component in the kit of parts, said article comprising a substrate, such as a sponge or a wipe comprising an aminosilicone.

DETAILED DESCRIPTION OF THE INVENTION

The Benefit

The present invention provides the benefit of increased or enhanced colour perception of artificially coloured or bleached hair without the use of further dyes or chromophores or bleaches. To those skilled in the art it will be obvious that other terminology can be used to describe this optical improvement/colour enhancement, including but not limited to: "increased colour intensity", "improved colour benefit", "chroma shift", "increase colour tonality", "increased colourfulness", "increased colour brightness", "increased colour vibrancy", "increased colour richness". And various marketing lines can be developed to communicate the benefit to consumers such as "enhances subtle hair tones and provides a natural hair colour", "removes dullness and allows true colour to shine through", "provides brighter highlights", "healthy colour", "more textured colour".

As used herein, the expressions "artificially coloured hair", and all related terms such as "coloured" and "colouring", and the like, are to be understood in their broad sense, i.e. as encompassing the actual colouring of hair as well as the mere bleaching of hair.

With the preferred compositions herein which are solutions of aminosilicones, the effect of improved colour perception of artificially coloured hair is particularly durable, over several wash cycles. Since consumers who colour their hair typically colour it every 4 to 6 weeks, there may not be a need for a new application of silicone in between two colourings. Consumers may however choose to apply aminosilicones in between two colourings.

There are a number of industry-accepted ways to measure the enhancing of the perception of color in this context. The CIE L C h colour system is used as a standard method of measuring colour (ref: Industrial Colour Testing, p20, by Hans G. Volz, ISBN 3-527-30436-3). Using this method it is possible to assess the improvement in optical properties of hair fibres by monitoring the L and C values using for example a handheld spectrophotometer such as Minolta 3600d, which is based on diffuser measurement geometry. However, a more useful measure employed herein is the use of the Kubelka-Munk function K/S. This value is also an accepted method for assessing the colourimetric properties of materials (ref: Industrial Colour Testing, p98, by Hans G. Volz, ISBN 3-527-30436-3).

The Aminosilicones

The aminosilicones useful in the present invention include but are not limited to the following:

(I)

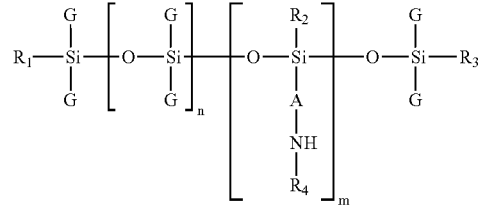

Wherein:

m and n are numbers with a sum (n+m) ranging from 2-2000, n is a number ranging from 1 to 1999, and m is a number ranging from 1 to 1999; and R1, R2, R3, which may be identical or different, are chosen from a hydroxyl radical, C1-C4 alkoxy radicals and methyl.

A is chosen from linear and branched C3-C8 alkenyl radicals.

R4 is chosen from H, phenyl, linear or branched C1-C4 alkyl radical, benzyl or preferably linear or branched (C2-C8) NH2. R4 can also contain amido groups or orther hetero atoms.

G is chosen from H, phenyl, hydroxyl, C1-C8 alkyl, preferably methyl.

Aminosilicone above may be of the random or block type.

(II) Aminosilicones with terminal amino groups:

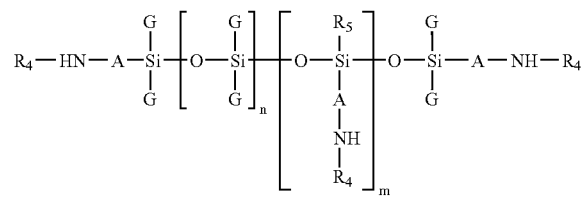

Wherein:

R1, R2, R4, A, G are defined as above; m and n are numbers with a sum (m+n) ranging from 1 to 2000, n is a number ranging from 1 to 1999 and m is a number ranging from 0 to 1999; R5=Me or A-NH—R4.

Aminosilicones above may be of the random or block type.

(III) Other aminosilicones which may be used in the compositions of the present invention are represented by the general formula:

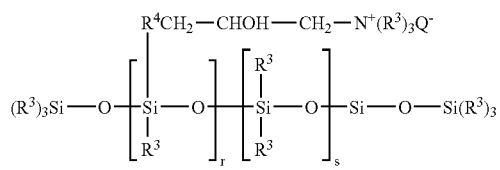

wherein $R^3$ is a monovalent hydrocarbon radical from $C_1$ to $C_{18}$, preferably an alkyl or alkenyl radical, such as methyl; $R^4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is a number from about 2 to about 20, preferably from about 2 to about 8; s is a number from about 20 to about 200, preferably from about 20 to about 50.

(IV) Cyclic structures:

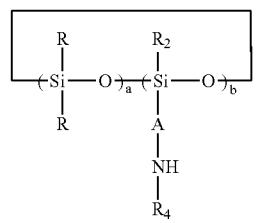

Where R is selected from alkyl group consisting of 1 to 10 carbon atoms and an aryl group consisting of 6 to 10 carbon atoms, R2, R4, A are defined above. Where a+b can be higher than 4, and b is different than 0.

(V) Organomodified silicones of the pendant or graft type wherein polar functional substituents are incorporated within or onto monovalent organic groups, $A^1$, $A^2$, $A^3$ and $A^4$ used hereinafter, as

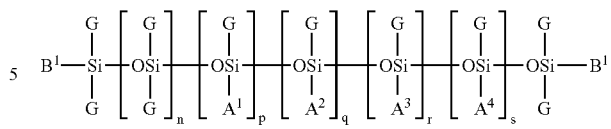

follows:

(VI) Also included are the organomodified silicones of the block copolymer type wherein these polar functional substituents are incorporated within or onto bivalent organic groups, $A^1$, $A^2$, $A^3$ and $A^4$ used hereinafter.

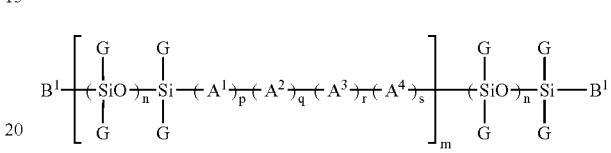

Where m is greater than or equal to 1, n is about 50 to 2000, p is about 0 to 50, q is about 0 to 50, r is about 0 to 50, s is about 0 to 50, wherein p+q+r+s is greater than or equal to 1, $B^1$ is H, OH, an alkyl or an alkoxy group. G is chosen from H, Phenyl, Hydroxyl, C1-C8 alkyl, preferably methyl.

The above functionalized silicones of the random or block copolymer type can also incorporate silicone branching groups including $MeSiO_{3/2}$, known as silsesquioxane or T groups, and $SiO_{4/2}$, known as Q groups by those skilled in the art.

Organic groups $A^1$, $A^2$, $A^3$ and $A^4$ may be straight, branched or mono- or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P and can incorporate one or more polar substituents selected from electron withdrawing, electron neutral, or electron donating groups with Hammett sigma para values between −1.0 and +1.5 which can be non-ionic, zwitterionic, cationic or anionic comprising, for example, groups $\alpha^1$, $\alpha^2$, $\alpha^3$, and $\alpha^4$ as defined below; S-linked groups including $S\alpha^1$, SCN, $SO_2\alpha^1$, $SO_3\alpha^1$, $SS\alpha1^1$, $SO\alpha^1$, $SO_2N\alpha^1\alpha^2$, $SN\alpha^1\alpha^2$, $S(N\alpha^1)\alpha^2$, $S(O)(N\alpha^1)\alpha^2$, $S\alpha^1(N\alpha^2)$, $SON\alpha^1\alpha^2$; O-linked groups including $O\alpha^1$, $OO\alpha^1$, OCN, $ON\alpha^1\alpha^2$; N-linked groups including $N\alpha^1\alpha^2$, $N\alpha^1\alpha^2\alpha^3+$, NC, $N\alpha^1O\alpha^2$, $N\alpha^1S\alpha^2$, NCO, NCS, $NO_2$, $N=N\alpha^1$, $N=NO\alpha^1$, $N\alpha^1CN$, $N=C=N\alpha^1$, $N\alpha^1N\alpha^2\alpha^3$, $N\alpha^1N\alpha^2N\alpha^3\alpha^4$, $N\alpha^1N=N\alpha^2$; other miscellaneous groups including COX, $CON_3$, $CON\alpha^1\alpha^2$, $CON\alpha^1CO\alpha^2$, $C(=N\alpha^1)N\alpha^1\alpha^2$, CHO CHS, CN, NC, and X; and at least one of $A^1$, $A^2$, $A^3$ and $A^4$ must contain an amine functionality.

$\alpha^1$, $\alpha^2$, $\alpha^3$, and $\alpha^4$ may be straight, branched or mono or polycyclic aliphatic, mono or polyunsaturated alkyl, aryl, heteroalkyl, heteroaliphatic or heteroolefinic moiety comprising 3 to 150 carbon atoms together with 0-50 heteroatoms, especially O, N, S, P.

X is F, Cl, Br, or I.

H is hydrogen, 0 is oxygen, N is nitrogen, C is carbon, S is ulphat, Cl is chlorine, Br is bromine, I is iodine, F is fluorine.

Hammett sigma para values are discussed in Römpp Chemie Lexikon, Georg Thieme Verlag, Stuttgart, N.Y., 9th Edition, 1995 under "Hammett Gleichung".

Preferred polar functional substituents for use in the present invention as described include, but are not limited to, polyoxyalkylene (polyether), primary and secondary amine, amide, quaternary ammonium, carboxyl, sulfonate, ulphate, carbohydrate, phosphate, and hydroxyl. More preferably, the polar functional substituents of the present invention include, but are not limited to polyoxyalkylene, primary and secondary amine, amide and carboxyl.

Another highly preferable polar functional substituents are amine-, polyol-type of the formula

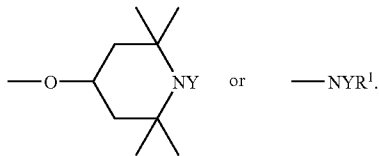

wherein each $R^1$ is independently selected from the group consisting of a hydrogen atom and a group of formula $—R^2NY_2$, each Y is independently a hydrogen atom or Y', and each Y' is a group of formula

Wherein $R^2$ is independently a divalent hydrocarbon group having 1 to 10 carbon atoms, and the proviso that every Y is not H.

More preferably $Y^1$ is a group of the formula $—CH_2CH(OH)CH_2OH$ and the functionalised silicone is of the pendant type, wherein n is from 200 to 500, p is from 20 to 50 and q, r and s are equal to zero.

Suitable functionalized silicones of the present invention include, but are not limited to, organomodified silicones with amine functionality available commercially under the trade names such as ADM1100 and ADM1600 from Wacker Silicones, DC2-8211, DC2-8822, DC2-8822A, DC8803, DC2-8040, DC2-8813, DC2-8630 and DC2-8566 from Dow Corning Corporation, KF-862, KF-861, KF-862S, KF-8005, KF-8004, KF-867S, KF-873, and X-52-2328 from Shin-Etsu Corporation, and TSF 4702, TSF 4703, TSF 4704, TSF 4705, TSF 4707, TSF 4708, TSF 4709, F42-B3115, SF 1708, SF 1923, SF 1921, SF 1925, OF TP AC3309, OF 7747, OF—NH TP AI3631, OF—NH TP AI3683 from GE Bayer Silicones.

VII) Other suitable aminosilicones for use herein have been disclosed in U.S. Pat. No. 5,792,825.

VIII) Other suitable aminosilicones for use herein have been disclosed in U.S. Pat. No. 6,136,215.

The aminosilicones herein can be used together with a durability additive. The durability additive is capable of modifying the functionalized silicones to render them more durable on polar fibrous substrates, especially where the substrate is hair that has been previously damaged through chemical treatments, such as occurs during permanent dyeing, bleaching and permanent waving. The durability additive must be miscible with the functionalized silicone wherein the mixture has a $(Tan\ \delta)^{-1}$ greater than zero, and:

$Tan\ \delta = G''/G'$

G' is the storage modulus

G'' is the loss modulus

Tan δ describes the ratio of energy lost to energy stored, where $Tan\ \delta = G''/G'$, G'' is the loss modulus and G' is the storage modulus. G'' and G' are established by means of the dynamic rheological properties, which, in turn, are measured by an oscillation sweep on a rheometer. More information on the measurement of dynamic rheological properties can be found in "Rheological Properties of Cosmetics and Toiletries" by Dennis Laba, Cosmetic Science and Technology Series, Volume 13, Marcel Dekker, Inc., ISBN 0-8247-9090-1.

For the avoidance of doubt, $(Tan\ \delta)^{-1}$ is directly equivalent to $1/(Tan\ \delta)$.

Preferably, the durability additive according to the invention comprises one or more organosiloxane resins. Without wishing to be bound by theory, organosiloxane resins are believed to create a 3-dimensional network within the functionalized silicone fluid giving rise to vicoelasticity thereby improving the adhesive properties of the fluid and hence the durability on a fibrous substrate. Preferably, the organosiloxane resin is insoluble in water.

Organosiloxane resins which my be included in the durability additive according to the invention comprise combinations of $R_3SiO_{1/2}$ "M" units, $R_2SiO$ "D" units, $RsiO_{3/2}$ "T" units, $SiO_2$ "Q" units in ratios to each other that satisfy the relationship $R_nSiO_{(4-n)/2}$ where n is a value between 1.0 and 1.50 and R is chosen from C1-C4 lower alkyl radicals such as methyl and a phenyl radical. Silanol or alkoxy functionalities may also be present in the resin structure.

More preferably, the organosiloxane resins comprise repeating monofunctional $R_3SiO_{1/2}$ "M" units and the quadrafunctional $SiO_2$ "Q" units, otherwise known as "MQ" resins. In this case, the ratio of the "M" to "Q" functional units is advantageously from 0.7 and the value of n is 1.2.

Organosiloxane resins such as these are commercially available as SR1000 available from GE Bayer Silicones and Wacker 803 from Wacker Silicones.

Advantageously, the organosiloxane resins according to the invention are solid at about 25° C. and have a molecular weight range of from 1,000 to 10,000 grams/mole.

The Composition is a Solution of the Aminosilicone

In the preferred embodiments of the invention, the aminosilicone herein is provided in the form of a solution, in contrast to emulsions, which are most commonly used in this technical field. The silicone solutions herein can comprise from 3% to 50% by weight of the total composition of an aminosilicone or mixtures thereof, preferably from 3% to 30%, more preferably from 3% to 10%, most preferably 4% to 10%.

Suitable organic solvents in which the aminosilicones herein can be dissolved in are selected from; volatile silicones, light liquid isoparafins, non-polar volatile oils, lower alkyl alcohols and polyhydric alcohols.

Non-polar, volatile liquid silicone oils are disclosed in U.S. Pat. No. 4,781,917. Additionally, a description of various volatile silicones materials is found in Todd et al., "Volatile Silicone Fluids for Cosmetics", Cosmetics and Toiletries, 91:27-32 (1976). Volatile silicones are selected from those that have linear or cyclic structures or a combination of both. Volatile silicone oils are selected from the group consisting of cyclic volatile silicones corresponding to the formula (V):

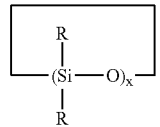

Where each R is independently selected from an alkyl group consisting of 1 to 10 carbon atoms and an aryl group consisting of 6 to 10 carbon atoms; and x has the value of 3 to 7;

Preferred volatile silicones are those with a linear structure corresponding to the formula (VI):

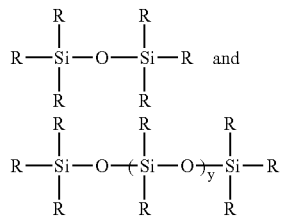

Where R is as described above and y has the value of 1 to 7.

Linear volatile silicones generally have a viscosity of less than about 5 centistokes at 25° C., whereas the cyclic silicones have viscosities of less than about 10 centistokes at 25° C. Examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

More preferred are dimethicones of varying viscosities e.g. DC200 (0.65-2cSt).

The volatile silicones suitable for use herein are commercially available or produced from known methods. Products useful include, but are not limited to, Hexamethyldisiloxane, octamethyltrisiloxane, decamethyltetrasiloxane, hexamethylcyclotrisiloxane, octamethylcyclotetrasiloxane, decamethylcyclopentasiloxane, low viscosity trimethyl endblocked polydimethylsiloxanes, cyclomethicone, dimethicone, polydimethyl cyclic siloxanes and mixtures thereof.

The lower alkyl alcohols useful herein are monohydric alcohols having 1 to 6 carbons, preferably ethanol and isopropanol. The polyhydric alcohols useful herein include propylene glycol, hexylene glycol, glycerin, and propane diol.

Non-polar, volatile oils particularly useful in the present invention are selected from the group consisting of silicone oils, hydrocarbons, and mixtures thereof. Such non-polar, volatile oils are disclosed, for example, in Cosmetics, Science, and Technology, Vol. 1, 27-104. The non-polar, volatile oils useful in the present invention may be either saturated or unsaturated, have an aliphatic character and be straight or branched chained or contain alicyclic or aromatic rings. Examples of preferred non-polar, volatile solvents include isododecane and isodecane (e.g., Permethyl-99A which is available from Presperse Inc.), C7-C8 through C12-C15 isoparaffins (such as the Isopar Series available from Exxon Chemicals), Octyl methicone (e.g. Silsoft 034), Hexyl methicone, Caprylyl methicone, Phenyl trimethicone, Diethyleneglycol hexyl ether, Diethyleneglycol n-butyl ether acetate, Ethyleneglycol hexyl ether, Ethylene glycol n-butyl ether acetate, Ethyleneglycol phenyl ether, Dipropylene glycol n-butyl ether, Propylene glycol phenyl ether.

The compositions herein may further comprise optional ingredients as long as the benefit materials or the adjuncts do not eliminate or substantially reduce the performance or shelf life of the composition. The additional ingredients may include, for example fragrances, vitamins, anionic, cationic, non-ionic, amphoteric or zwitterionic surfactants; stabilizers, cationic polymers, non-ionic polymers, anionic polymers, complex coacervate capsules, polymeric thickeners, oils, emollients, humectants, moisturizers, preservatives, herb and plant extracts, chelators, UV filters, and other common adjuvants well known to those skilled in the art.

However, it is to be noted that the invention herein, in its broadest sense, is not limited to the use of solutions of aminosilicones. The solutions of aminosilicones provide a benefit of maximum intensity and durability, however the person skilled in the art could also choose to formulate the aminosilicones in, for instance, a conditioner that would typically be an emulsion. The aminosilicone could then be the only silicone in the conditioner, or there could be another, non-amino silicone. In such a case where the aminosilicone is formulated as or into a conditioner, the conditioner would then provide a conditioning benefit as well as a colour enhancement benefit, albeit one of lesser intensity and/or durability.

The Kit of Parts

In one embodiment of this invention there is provided a kit-of parts. Indeed, the compositions of the invention may be provided to the consumer as a stand-alone product, for instance for use in between two colourings. However, the compositions are most conveniently applied immediately after colouring, as further explained in the "method" description below. Therefore, a preferred embodiment of the inventions is a kit-of parts comprising the traditional components of a hair colouring kit, plus an additional component that comprises an aminosilicone. This additional component is preferably formulated as a solution of the aminosilicone, i.e. the additional component is preferably provided as a composition according to the invention. And this additional component is preferably provided as an article of manufacture as further explained below, or as a spray.

Typically, during the process of oxidative dyeing, two components are provided which are mixed together prior to application to the hair. The first component usually comprises an oxidising agent, such as hydrogen peroxide, and the second component comprises a dyeing material, such as an oxidative dye precursor and a coupler (buffered at a high Ph, typically around 10). After contacting with the hair, the mixture is left for a period of time suitable to allow the required color transformation to occur. A discussion of oxidation dyeing of hair can be found in "The Science of Hair Care" by Charles Zviak, Marcel Dekker, New York, 1986. In this case, the kit of parts according to the invention would comprise such first and second components, a well as a third component comprising an aminosilicone. Typically a separate conditioner is supplied within the colorant kit, designed to be applied to wet hair after the colorant has been rinsed, and the kit of part of the invention would, in this preferred embodiment, comprise said first and second colouring components, a third component which is the conditioner, and a fourth component comprising an aminosilicone.

The Article of Manufacture

In one of its embodiments, the present invention encompasses an article of manufacture that is a substrate such as a wipe, or a sponge, and which comprises an aminosilicone, as described above, preferably a composition which is a solution of the silicone, as described above.

Non limiting examples of suitable wipes and sponges include non woven substrates, woven substrates, hydroentangled substrates, air entangled substrates, natural sponges, synthetic sponges, polymeric nettled meshes, formed films, thermal bonded substrates, chemical bonded substrates, and the like. The substrate may be made in a variety of shapes and forms including flat pads, thick pads, thin sheets, ball shaped implements, irregularly shaped implements, and having sizes ranging from a surface area of about a square inch to about hundreds of square inches. The exact size will depend on the desired use and product characteristics. There is also considerable art addressing wipes and sponges, in particular wipes or sponges for delivering substances to a surface, see for example WO 99/66793, U.S. 2003/0035824, U.S. 2003/0086962, and U.S. Pat. No. 6,338,855. Any of such known wipes or sponges are suitable for use herein. It is believed that the substrate delivers an effective amount of the aminosilicone(s) in a controlled manner.

Typically, suitable wipes or sponges for use herein are loaded with the aminosilicone composition at a weight ratio of composition to wipe of from 1:4 to 4:1. The aminosilicone is preferably loaded onto the substrate, but in another embodiment a substrate is provided together with a separately packaged aminosilicone, and the aminosilicone is loaded onto the substrate shortly or immediately before use.

In another embodiment, the article of manufacture herein is a comb or a brush which is impregnated with or releasably contains the aminosilicone.

Method of Use:

In a further embodiment of the invention there is provided a method if use of the aminosilicone or composition herein. The aminosilicone or composition of the invention can be applied at any time to enhance the colour perception of artificially colored hair. It can be applied on dry or wet hair, preferably dry by any suitable means. But for reasons of convenience, the silicone or compositions of the invention are applied onto artificially colored hair right after it has been colored preferably but also other times. Therefore, in a more preferred embodiment of the invention, there is a method of use where hair is first colored, then rinsed, then optionally conditioned and then rinsed, then dried, and then the a composition of the invention is applied onto said coloured hair.

EXAMPLES

| Material | % in composition 1 | % in composition 2 |
|---|---|---|
| ADM1100 (Supplied by Waker Co) | 30 | 5 |
| DC200 (5 cSt) (Supplied by Dow Corning) | 70 | 95 |

| Material | % in composition 3 | % in composition 4 |
|---|---|---|
| DC2-8566 (Supplied by Dow Corning) | 20 | 10 |
| Permethyl 99 (supplied by Chesham Chemicals Limited) | 80 | 90 |

| Material | % in composition 5 | % in composition 6 |
|---|---|---|
| SF-1708 (Supplied by General Electric) | 25 | 15 |
| Isopropyl alcohol (supplied by Shell) | 75 | 85 |

6 g compositions 1, 2, 3 or 4 is then applied to a substrate for use on artificially coloured hair.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing form the spirit and scope of the invention. It is therefore intended to cover in the appended claims all such changes and modifications that are within the scope of this invention.

What is claimed is:

1. A method of enhancing the colour perception of artificially coloured hair comprising applying a composition comprising an effective amount of an aminosilicone onto said hair, wherein said aminosilicone is selected from the group consisting of silicones according to the formulas (I) to (IV) and mixtures thereof:

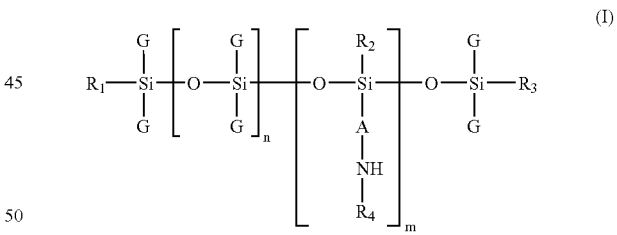

Wherein:

m and n are numbers wit a sum (n+m) ranging from about 2 to about 2000, n is a number ranging from about 1 to about 1999, and m is a number ranging from about 1 to about 1999; and R1, R2, R3, which may be identical or different, are chosen from a hydroxyl radical, C1-C4 alkoxy radicals or methyl, A is chosen from linear or branched C3-C8 alkenyl radicals, R4 is chosen from H, phenyl, linear or branched C1-C4 alkyl radical, benzyl, or a linear or branched (C2-C8) NH2;

G is chosen from H, phenyl, hydroxyl, or a C1-C8 alkyl;

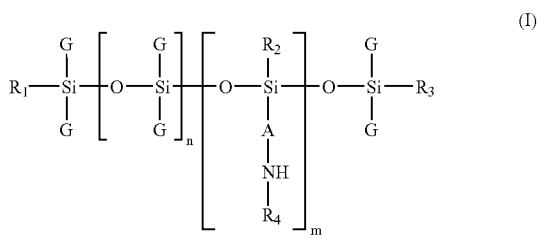

(I)

Wherein;

m and n are numbers with a sum (n+m) ranging from about 2 to about 2000, n is a number ranging from about 1 to about 1999, and m is a number ranging from about 1 to about 1999; and R1, R2, R3, which may be identical or different, are chosen from a hydroxyl radical, C1-C4 alkoxy radicals or methyl, A is chosen from linear or branched C3-C8 alkenyl radicals, R4 is chosen from H, phenyl, linear or branched C1-C4 alkyl radical, benzyl, or a linear or branched (C2-C8) NH2;

G is chosen from H, phenyl, hydroxyl, or a C1-C8 alkyl;

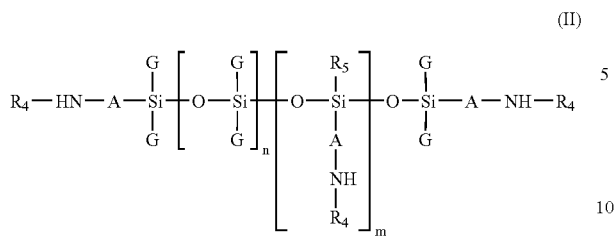

(II)

Wherein:

R1, R2, R4, A, G are defined as above; m and n are numbers with a sum (m+n) ranging from about 1 to about 2000, n is a number ranging from about 1 to about 1999 and m is a number ranging from 0 to about 1999, R5 is Me or A-NH—R4;

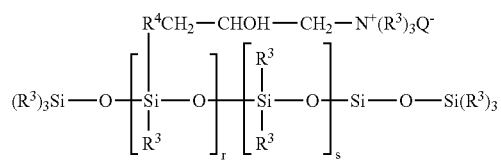

(III)

Wherein:

$R^3$ is a monovalent hydrocarbon radical from $C_1$ to $C_{18}$; $R^4$ is a hydrocarbon radical; $Q^-$ is a halide ion; r is a number from about 2 to about 20; s is a number from about 20 to about 200;

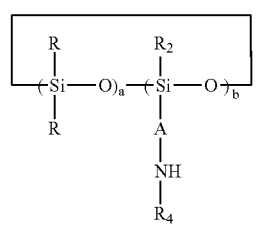

(IV)

Wherein:

R is selected from alkyl group consisting of about 1 to about 10 carbon atoms and an aryl group consisting of about 6 to about 10 carbon atoms; R2, R4, and A are as defined above;

Where a+b is greater than about 4, and b is different than 0.

2. A composition for enhancing the color perception of artificially colored hair comprising a solution of an aminosilicone selected from the group consisting of silicones according to the formulas (I) to (IV) and mixtures thereof, wherein said aminosilicone comprises from about 3% to about 50% by weight of the total composition of said solution:

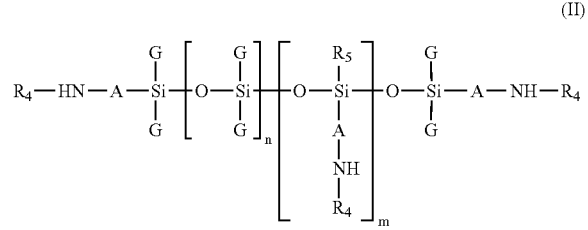

(II)

Wherein:

R1, R2, R4, A, G are defined as above; m and n are numbers with a sum (m+n) ranging from about 1 to about 2000, n is a number ranging from about 1 to about 1999 and m is a number ranging from 0 to about 1999, R5 is Me or A-NH—R4;

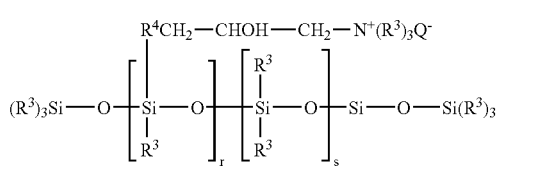

(III)

Wherein:

$R^3$ is a monovalent hydrocarbon radical from $C_1$ to $C_{18}$; $R^4$ is a hydrocarbon radical; $Q^-$ is a halide ion; r is a number from about 2 to about 20; s is a number from about 20 to about 200;

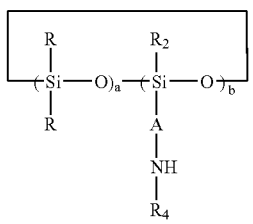
(IV)

Wherein:

Where R is selected from alkyl group consisting of about 1 to about 10 carbon atoms and an aryl group consisting of about 6 to about 10 carbon atoms; R2, R4, A are defined above;

Where a+b is greater than about 4, and b is different than 0.

3. A composition according to claim 2, wherein said solution comprises an aminosilicone and a solvent for said aminosilicone, wherein said solvent is selected from the group consisting of volatile silicones, light liquid isoparafins, non polar volatile oils, lower alkyl alcohols and polyhydric alcohols, and mixtures thereof.

4. A composition according to claim 2 wherein said aminosilicone comprises from about 3% to about 10% by weight of the total composition.

5. A composition according to claim 3 wherein said aminosilicone comprises from about 3% to about 10% by weight of the total composition.

6. A method of enhancing the colour perception of artificially coloured hair comprising applying the composition of claim 2 onto said hair.

7. A method of enhancing the colour perception of artificially coloured hair comprising applying the composition of claim 3 onto said hair.

8. A method of enhancing the colour perception of artificially coloured hair comprising applying the composition of claim 4 onto said hair.

9. A method of enhancing the colour perception of artificially coloured hair comprising applying the composition of claim 2 onto said hair, which comprises the steps of:
First, colouring hair; then
Rinsing said hair; then
Drying said hair, and then
Applying said composition onto said hair.

10. A method of enhancing the colour perception of artificially coloured hair comprising applying the composition of claim 3 onto said hair, which comprises the steps of:
First, colouring hair; then
Rinsing said hair; then
Drying said hair, and then
Applying said composition onto said hair.

11. A method of enhancing the colour perception of artificially coloured hair comprising applying the composition of claim 4 onto said hair, which comprises the steps of:
First, colouring hair; then
Rinsing said hair; then
Drying said hair, and then
Applying said composition onto said hair.

12. A kit of parts comprising one or several first components for coloring hair and a second component for enhancing the color perception of the hair colored with said first component, where said second component comprises an aminosilicone, and further, wherein said aminosilicone is in the form of a composition according to claim 2.

13. A kit of parts comprising one or several first components for coloring hair and a second component for enhancing the color perception of the hair colored with said first component, where said second component comprises an aminosilicone, and further, wherein said aminosilicone is in the form of a composition according to claim 3.

14. A kit of parts comprising one or several first components for coloring hair and a second component for enhancing the color perception of the hair colored with said first component, where said second component comprises an aminosilicone, and further, wherein said aminosilicone is in the form of a composition according to claim 4.

15. An article of manufacture comprising a wipe or a sponge comprising a silicone selected from the group consisting of silicones according to the formulas (I) to (VI) and mixtures thereof:

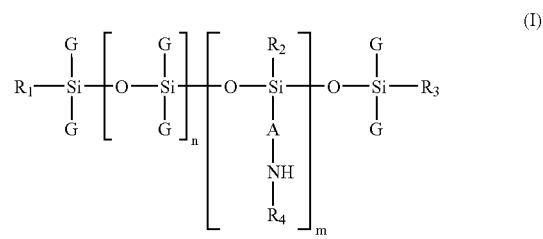
(I)

Wherein:

m and n are numbers with a sum (n+m) ranging from about 2 to about 2000, n is a number ranging from about 1 to about 1999, and m is a number ranging from about 1 to about 1999; and R1, R2, R3, which may be identical or different, are chosen from a hydroxyl radical, C1-C4 alkoxy radicals and methyl, A is chosen from linear and branched C3-C8 alkenyl radicals, R4 is chosen from H, phenyl, linear or branched C1-C4 alkyl radical, benzyl or preferably linear or branched (C2-C8)NH2;

G is chosen from H, phenyl, hydroxyl, C1-C8 alkyl;

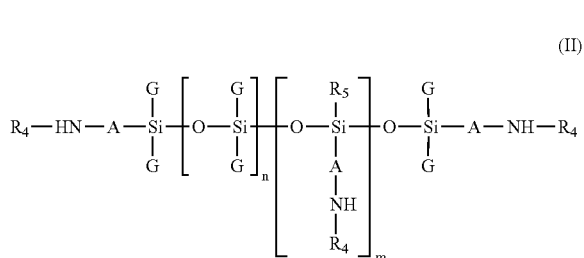
(II)

Wherein:

R1, R2, R4, A, G are defined as above; m and n are numbers with a sum (m+n) ranging from about 1 to about 2000, n is a number ranging from about 1 to about 1999 and m is a number ranging from 0 to about 1999, R5 is Me or A-NH—R4;

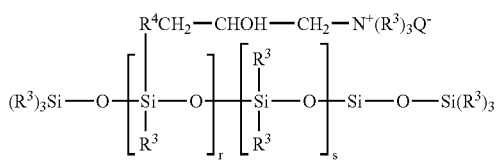

(III)

Wherein:
R³ is a monovalent hydrocarbon radical from $C_1$ to $C_{18}$;
R⁴ is a hydrocarbon radical; $Q^-$ is a halide ion; r is a number from about 2 to about 20; s is a number from about 20 to about 200;

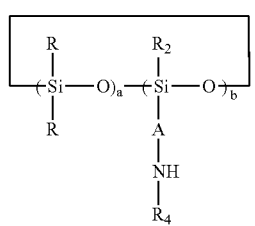

(IV)

Wherein:
R is selected from alkyl group consisting of about 1 to about 10 carbon atoms or aryl group consisting of about 6 to about 10 carbon atoms, R2, R4, A are defined above;
Where a+b is greater than about 4, and b is different than 0.

(V) Organomodified silicones of the pendant or graft type wherein polar functional substituents are incorporated within or onto monovalent organic groups, and $A^1$, $A^2$, $A^3$, $A^4$, n, p, q, r, s, $B^1$ and G are as defined below;

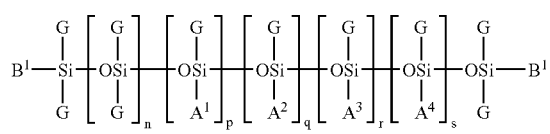

Wherein n is about 50 to 2000, p is about 0 to 50, q is about 0 to 50, r is about 0 to 50, s is about 0 to 50, and wherein p+q+r+s is greater than or equal to 1, $B^1$ is H, hydroxyl, an alkyl or an alkoxy group, G is chosen from H, phenyl, hydroxyl, or C1-C8 alkyl; and $A^1$, $A^2$, $A^3$ and $A^4$ are straight, branched or mono- or polycyclic aliphatic, mono or polyunsaturated alkyl, aryl, heteroalkyl, heteroaliphatic or heteroolefinic moieties comprising 3 to 150 carbon atoms together with 0-50 heteroatoms, ax least one of $A^1$, $A^2$, $A^3$ and $A^4$ contains an amine functionality, and $A^1$, $A^2$, $A^3$, and $A^4$ include at least one polar substituent selected from electron withdrawing, electron neutral, or electron donating groups, said groups having Hammett sigma para values between −1.0 and +1.5, or selected from $\alpha^1$, $\alpha^2$, $\alpha^3$, $\alpha^4$, $S\alpha^1$, $SCN$, $SO_2\alpha^1$, $SO_3\alpha^1$, $SS\alpha 1^1$, $SO\alpha^1$, $SO_2N\alpha^1\alpha^2$, $SN\alpha^1\alpha^2$, $S(N\alpha^1)$ $\alpha^2$, $S(O)(N\alpha^1)$ $\alpha^2$, $S\alpha^1(N\alpha^2)$, $SON\alpha^1\alpha^2$, $O\alpha^1$, $OO\alpha^1$, $OCN$, $ON\alpha^1\alpha^2$, $N\alpha^1\alpha^2$, $N\alpha^1\alpha^2\alpha^3+$, $NC$, $N\alpha^1O\alpha^2$, $N\alpha^1S\alpha^2$, $NCO$, $NCS$, $NO_2$, $N=N\alpha^1$, $N=NO\alpha^1$, $N\alpha^1CN$, $N=C=N\alpha^1$, $N\alpha^1N\alpha^2\alpha^3$, $N\alpha^1N\alpha^2N\alpha^3\alpha^4$, $N\alpha^1N=N\alpha^2$, $COX$, $CON_3$, $CON\alpha^1\alpha^2$, $CON\alpha^1CO\alpha^2$, $C(=N\alpha^1)N\alpha^1\alpha^2$, $CHO$, $CHS$, $CN$, $NC$, and $X$, wherein $\alpha^1$, $\alpha^2$, $\alpha^3$, and $\alpha^4$ are straight, branched or mono- or polycyclic aliphatic, mono or polyunsaturated alkyl, aryl, heteroalkyl, heteroaliphatic or heteroolefinic moieties comprising 3 to 150 carbon atoms together with 0-50 heteroatoms, and X is F, Cl, Br, or I.

(VI) Organomodified silicones of the block copolymer type wherein polar functional substituents arc incorporated within or onto bivalent organic groups, and $A^1$, $A^2$, $A^3$, $A^4$, n, p, q, r, s, $B^1$, and G are as defined above:

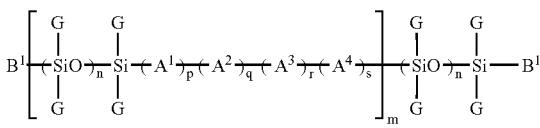

Wherein m is greater than or equal to 1.

16. An article of manufacture according to claim 15 wherein said silicone is in a solution, and further, wherein said silicone comprises from about 3% to about 50% by weight of said solution.

* * * * *